US012350086B2

(12) United States Patent
Fukuda

(10) Patent No.: US 12,350,086 B2
(45) Date of Patent: Jul. 8, 2025

(54) INFORMATION PROCESSING APPARATUS, INFORMATION PROCESSING METHOD, AND INFORMATION PROCESSING PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 294 days.

(21) Appl. No.: 18/177,554

(22) Filed: Mar. 2, 2023

(65) Prior Publication Data
US 2023/0200769 A1 Jun. 29, 2023

Related U.S. Application Data

(63) Continuation of application No. PCT/JP2021/030467, filed on Aug. 19, 2021.

(30) Foreign Application Priority Data

Sep. 28, 2020 (JP) .................. 2020-162694

(51) Int. Cl.
G06T 5/50 (2006.01)
A61B 6/00 (2006.01)
(Continued)

(52) U.S. Cl.
CPC .............. A61B 6/502 (2013.01); A61B 6/481 (2013.01); A61B 6/482 (2013.01); G06T 5/50 (2013.01);
(Continued)

(58) Field of Classification Search
CPC ........... A61B 6/00; A61B 6/481; A61B 6/482; A61B 6/486; A61B 6/502; A61B 6/5205;
(Continued)

(56) References Cited

U.S. PATENT DOCUMENTS

2006/0025680 A1  2/2006 Jeune-Iomme et al.
2012/0134464 A1  5/2012 Hoernig et al.
(Continued)

FOREIGN PATENT DOCUMENTS

DE   10 2011 087128 A1   5/2013
JP   2012-501750 A       1/2012
(Continued)

OTHER PUBLICATIONS

The extended European search report issued by the European Patent Office on Sep. 5, 2023, which corresponds to European Patent Application No. 21872042.3-1126 and is related to U.S. Appl. No. 18/177,554.

(Continued)

Primary Examiner — Jurie Yun
(74) Attorney, Agent, or Firm — Studebaker Brackett PLLC

(57) ABSTRACT

An information processing apparatus includes at least one processor that is configured to: acquire a low-energy image captured by a radiography apparatus by emitting radiation having first energy to a subject into which a contrast medium has been injected, and each of a plurality of high-energy images captured by the radiography apparatus at different timings by emitting radiation having second energy higher than the first energy to the subject into which the contrast medium has been injected, and generate a plurality of difference images showing a difference between the low-energy image and each of the plurality of high-energy images.

13 Claims, 10 Drawing Sheets

(51) Int. Cl.
*A61B 6/50* (2024.01)
*G06T 7/00* (2017.01)
*G06V 10/25* (2022.01)

(52) U.S. Cl.
CPC ............ *G06T 7/0012* (2013.01); *G06V 10/25* (2022.01); *G06T 2207/10116* (2013.01); *G06T 2207/20224* (2013.01); *G06T 2207/30068* (2013.01)

(58) Field of Classification Search
CPC ... A61B 6/5217; A61B 6/5235; A61B 6/0414; G06T 5/50; G06T 7/00; G06T 7/0012; G06T 7/0016; G06T 2207/10116; G06T 2207/20224; G06T 2207/30068; G06V 10/25; G06V 2201/03; G06V 2201/034
See application file for complete search history.

(56) References Cited

U.S. PATENT DOCUMENTS

| | | | |
|---|---|---|---|
| 2016/0235380 A1 | 8/2016 | Smith et al. | |
| 2023/0008465 A1 | 1/2023 | Smith et al. | |
| 2023/0200770 A1* | 6/2023 | Fukuda | A61B 6/5217 378/37 |
| 2023/0206412 A1* | 6/2023 | Fukuda | G06T 5/94 382/130 |
| 2023/0218254 A1* | 7/2023 | Fukuda | G06T 5/50 378/37 |

FOREIGN PATENT DOCUMENTS

| | | |
|---|---|---|
| JP | 2016-533803 A | 11/2016 |
| WO | 2010/028208 A1 | 3/2010 |
| WO | 2013/047193 A1 | 4/2013 |

OTHER PUBLICATIONS

Siemens AG et al., "Verfahren zum Bestimmen der Kontrastmittelkinetik fur Charakterisierung von Lasionen der Mamma in der kontrastverstarkten Tomosynthese", Prior Art Publishing GmbH, Manfred-von-Richthofen-Str. 9, 12101, Berlin, Germany, Sep. 24, 2020, pp. 1-3.

International Search Report issued in PCT/JP2021/030467; mailed Oct. 19, 2021.

International Preliminary Report On Patentability (Chapter I) and Written Opinion of the International Searching Authority issued in PCT/JP2021/030467; issued Mar. 28, 2023.

An Office Action; "Notice of Reasons for Refusal," mailed by the Japanese Patent Office on Jan. 9, 2024, which corresponds to Japanese Patent Application No. 2022-551200 and is related to U.S. Appl. No. 18/177,554; with English language translation.

* cited by examiner

INFORMATION PROCESSING APPARATUS, INFORMATION PROCESSING METHOD, AND INFORMATION PROCESSING PROGRAM

CROSS-REFERENCE TO RELATED APPLICATIONS

This application is a continuation application of International Application No. PCT/JP2021/030467, filed on Aug. 19, 2021, which is incorporated herein by reference in its entirety. Further, this application claims priority from Japanese Patent Application No. 2020-162694, filed on Sep. 28, 2020, the disclosure of which is incorporated by reference herein in their entirety.

BACKGROUND

Technical Field

The present disclosure relates to an information processing apparatus, an information processing method, and a non-transitory storage medium storing an information processing program.

Related Art

A technology of performing contrast imaging of capturing a low-energy image and a high-energy image by irradiating a subject into which a contrast medium has been injected with radiation having different energies and generating a difference image showing a difference between the high-energy image and the low-energy image to generate a radiation image in which the contrast medium is enhanced is known. For example, WO2013/047193A discloses a technology of displaying a difference image obtained by contrast imaging as a moving image.

By the way, in diagnosing a lesion or the like in a subject, it is desired to observe a temporal change of a contrast medium permeating a region of interest, such as a lesion, specifically, a temporal change of a contrast amount. In the technology disclosed in WO2013/047193A, since the difference image is displayed as the moving image, it is possible to observe the temporal change, but the number of radiation images captured in order to display the difference image as the moving image tends to be large.

SUMMARY

The present disclosure is made in view of the above circumstances, and provides an information processing apparatus, an information processing method, and a non-transitory storage medium storing an information processing program capable of observing a temporal change of a contrast amount with a smaller number of radiation images.

A first aspect of the present disclosure relates to an information processing apparatus comprising at least one processor, in which the processor acquires a low-energy image captured by a radiography apparatus by emitting radiation having first energy to a subject into which a contrast medium has been injected, and each of a plurality of high-energy images captured by the radiography apparatus at different timings by emitting radiation having second energy higher than the first energy to the subject into which the contrast medium has been injected, and generates a plurality of difference images showing a difference between the low-energy image and each of the plurality of high-energy images.

A second aspect of the present disclosure relates to the information processing apparatus according to the first aspect, in which the processor continuously displays the plurality of difference images as a moving image in a time series order of capturing.

A third aspect of the present disclosure relates to the information processing apparatus according to the first or second aspect, in which the processor displays a difference image having a highest contrast of a region of interest among the plurality of difference images.

A fourth aspect of the present disclosure relates to the information processing apparatus according to any one of the first to third aspects, in which the processor derives a contrast amount of a region of interest in each of the plurality of difference images, and generates information indicating a temporal change of the contrast amount of the region of interest and displays the generated information.

A fifth aspect of the present disclosure relates to the information processing apparatus according to the fourth aspect, in which the processor derives a contrast amount of a region outside the region of interest in each of the plurality of difference images, and generates information indicating a temporal change of the contrast amount of the region outside the region of interest and displays the generated information.

A sixth aspect of the present disclosure relates to the information processing apparatus according to the fourth or fifth aspect, in which the processor receives information indicating the region of interest or information indicating a region outside the region of interest, and derives the contrast amount based on the received information.

A seventh aspect of the present disclosure relates to the information processing apparatus according to any one of the first to sixth aspects, in which the processor acquires, as the low-energy image, a plurality of low-energy images captured by the radiography apparatus at different timings, which are smaller than in capturing of the high-energy images, and generates a difference image showing a difference between each of the plurality of high-energy images and a low-energy image satisfying a predetermined condition among the plurality of low-energy images.

An eighth aspect of the present disclosure relates to the information processing apparatus according to the seventh aspect, in which the predetermined condition is a condition in which an imaging timing is closest to an imaging timing of the high-energy image.

A ninth aspect of the present disclosure relates to the information processing apparatus according to the seventh or eighth aspect, in which an imaging interval between the plurality of low-energy images is determined according to the subject.

A tenth aspect of the present disclosure relates to the information processing apparatus according to the seventh or eighth aspect, in which a ratio between the number of the plurality of low-energy images and the number of the plurality of high-energy images is determined according to the subject.

An eleventh aspect of the present disclosure relates to the information processing apparatus according to any one of the first to sixth aspects, in which the processor generates a first difference image showing a difference between the low-energy image and a high-energy image having an imaging timing closest to an imaging timing of the low-energy image, generates a second difference image showing a difference between the high-energy images, and generates the plurality of difference images by using the first difference image and the second difference image.

A twelfth aspect of the present disclosure relates to the information processing apparatus according to any one of the first to eleventh aspects, in which the subject is a breast, and the radiography apparatus is a mammography apparatus.

In addition, a thirteenth aspect of the present disclosure relates to an information processing method executed by a computer, the method comprising acquiring a low-energy image captured by a radiography apparatus by emitting radiation having first energy to a subject into which a contrast medium has been injected, and each of a plurality of high-energy images captured by the radiography apparatus at different timings by emitting radiation having second energy higher than the first energy to the subject into which the contrast medium has been injected, and generating a plurality of difference images showing a difference between the low-energy image and each of the plurality of high-energy images.

In addition, a fourteenth aspect of the present disclosure relates to a non-transitory storage medium storing a program executable by a computer to perform information processing, the information processing comprising acquiring a low-energy image captured by a radiography apparatus by emitting radiation having first energy to a subject into which a contrast medium has been injected, and each of a plurality of high-energy images captured by the radiography apparatus at different timings by emitting radiation having second energy higher than the first energy to the subject into which the contrast medium has been injected, and generating a plurality of difference images showing a difference between the low-energy image and each of the plurality of high-energy images.

According to the present disclosure, it is possible to observe the temporal change of the contrast amount with a smaller number of radiation images.

DETAILED DESCRIPTION

In the following, an embodiment of the present invention will be described in detail with reference to the drawings. It should be noted that the present embodiment does not limit the present invention.

Figure 1:
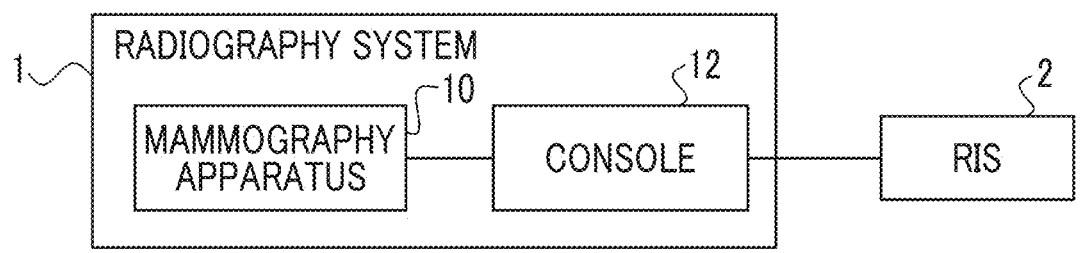
FIG. 1 is a configuration diagram schematically showing an example of an overall configuration of a radiography system according to an embodiment.

First, an example of an overall configuration of a radiography system according to the present embodiment will be described. FIG. 1 shows a configuration diagram showing an example of an overall configuration of a radiography system 1 according to the present embodiment. As shown in FIG. 1, the radiography system 1 according to the present embodiment comprises a mammography apparatus 10 and a console 12. The mammography apparatus 10 according to the present embodiment is an example of a radiography apparatus according to the present disclosure. In addition, the console 12 according to the present embodiment is an example of an information processing apparatus according to the present disclosure.

Figure 2:
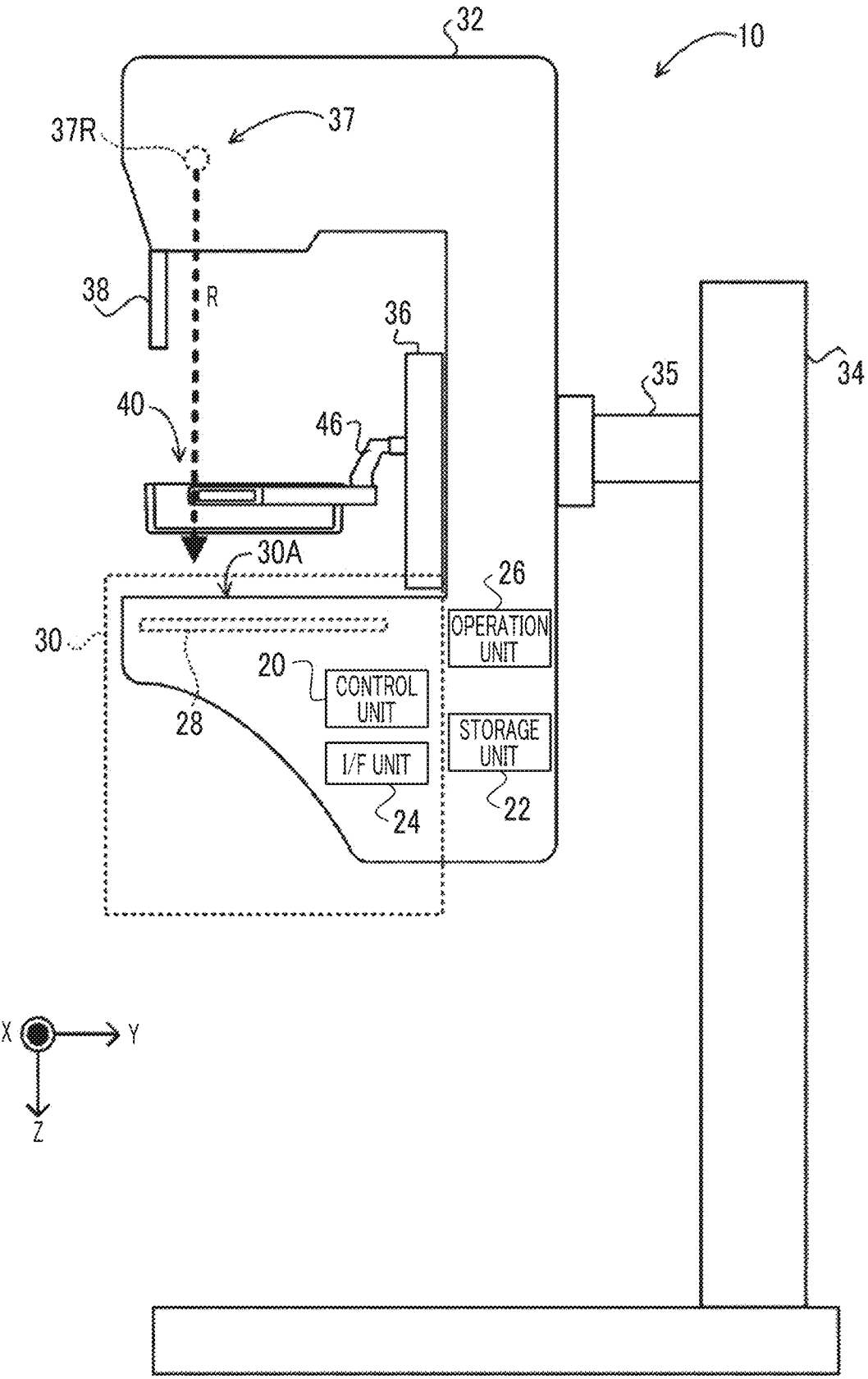
FIG. 2 is a side view showing an example of an appearance of a mammography apparatus according to the embodiment.

First, the mammography apparatus 10 according to the present embodiment will be described. FIG. 2 shows a side view showing an example of an appearance of the mammography apparatus 10 according to the present embodiment. It should be noted that FIG. 2 shows the example of the appearance of the mammography apparatus 10 as viewed from a right side of an examinee.

The mammography apparatus 10 according to the present embodiment is an apparatus that uses a breast of the examinee as a subject and captures a radiation image of the breast by irradiating the breast with radiation R (for example, X-rays). It should be noted that the mammography apparatus 10 may be an apparatus that images the breast of the examinee in a state in which the examinee is sitting on a chair (including a wheelchair) or the like (sitting state) in addition to a state in which the examinee is standing (standing state).

In addition, the mammography apparatus 10 according to the present embodiment has a function of performing two types of imaging of so-called contrast imaging in which the imaging is performed in a state in which a contrast medium has been injected into the breast of the examinee and general imaging. It should be noted that, in the present embodiment, the imaging to be performed in a state in which the contrast medium has been injected into the breast of the examinee refers to the "contrast imaging", and the imaging that is not the contrast imaging refers to the "general imaging".

As shown in FIG. 2, the mammography apparatus 10 according to the present embodiment comprises a control unit 20, a storage unit 22, and an interface (I/F) unit 24 inside the imaging table 30. The control unit 20 controls an overall operation of the mammography apparatus 10 under the control of the console 12. The control unit 20 comprises a central processing unit (CPU), a read only memory (ROM), and a random access memory (RAM) (all not shown). The ROM stores, in advance, various programs, including an imaging processing program for performing control related to radiation image capturing, which is executed by the CPU. The RAM transitorily stores various data.

The storage unit 22 stores the image data of the radiation image captured by the radiation detector 28 or various types of other information. Specific examples of the storage unit 22 include a hard disk drive (HDD) and a solid state drive (SSD). The I/F unit 24 performs communication of various types of information with the console 12 by wireless communication or wired communication. The image data of the radiation image captured by the radiation detector 28 in the mammography apparatus 10 is transmitted to the console 12 via the I/F unit 24 by wireless communication or wired communication.

In addition, an operation unit 26 is provided as a plurality of switches on an imaging table 30 of the mammography apparatus 10, for example. It should be noted that the operation unit 26 may be provided as a touch panel type switch, or may be provided as a foot switch operated by a user, such as a doctor or an engineer with a foot.

The radiation detector 28 detects the radiation R that has passed through the breast which is the subject. In addition, as shown in FIG. 2, the radiation detector 28 is disposed inside the imaging table 30. In the mammography apparatus 10 according to the present embodiment, the user positions the breast of the examinee on an imaging surface 30A of the imaging table 30 in a case of performing the imaging.

The radiation detector 28 detects the radiation R transmitted through the breast of the examinee and the imaging table 30, generates a radiation image based on the detected radiation R, and outputs image data representing the generated radiation image. A type of the radiation detector 28 according to the present embodiment is not particularly limited. For example, a radiation detector of an indirect conversion method that converts the radiation R into light and converts the converted light into a charge may be used, and a radiation detector of a direct conversion method that directly converts the radiation R into a charge may be used.

A radiation emitting unit 37 comprises the radiation source 37R. As shown in FIG. 2, the radiation emitting unit 37 is provided in an arm part 32 together with the imaging table 30 and the compression unit 36. As shown in FIG. 2, a face guard 38 is attachable and detachable at a position near the examinee on the arm part 32 below the radiation emitting unit 37. The face guard 38 is a protective member for protecting the examinee from the radiation R emitted from the radiation source 37R.

It should be noted that, as shown in FIG. 2, the mammography apparatus 10 according to the present embodiment comprises the arm part 32, a base 34, and a shaft part 35. The arm part 32 is held by the base 34 to be movable in a vertical direction (Z-axis direction). The shaft part 35 connects the arm part 32 to the base 34. In addition, the arm part 32 is rotatable relative to the base 34 with the shaft part 35 as a rotation axis.

The arm part 32, the imaging table 30, and the compression unit 36 can be separately rotated relative to the base 34 with the shaft part 35 as a rotation axis. In the present embodiment, the base 34, the arm part 32, the imaging table 30, and the compression unit 36 are each provided with an engaging part (not shown), and each of the arm part 32, the imaging table 30, and the compression unit 36 is connected to the base 34 by switching a state of the engaging part. One or two of the arm part 32, the imaging table 30, or the compression unit 36, which are connected to the shaft part 35, are integrally rotated around the shaft part 35.

The compression unit 36 is provided with a compression plate driving unit (not shown) that moves the compression plate 40 in the vertical direction (Z-axis direction). The compression plate 40 according to the present embodiment has a function of compressing the breast of the examinee. A support part 46 of the compression plate 40 is attachably and detachably attached to the compression plate driving unit, is moved in the vertical direction (Z-axis direction) by the compression plate driving unit, and compresses the breast of the examinee with the imaging table 30.

On the other hand, the console 12 according to the present embodiment has a function of controlling the mammography apparatus 10 by using an imaging order and various types of information acquired from a radiology information system (RIS) 2 via a wireless communication local area network (LAN) and the like, and an instruction performed by the user by an operation unit 56 and the like.

Figure 3:
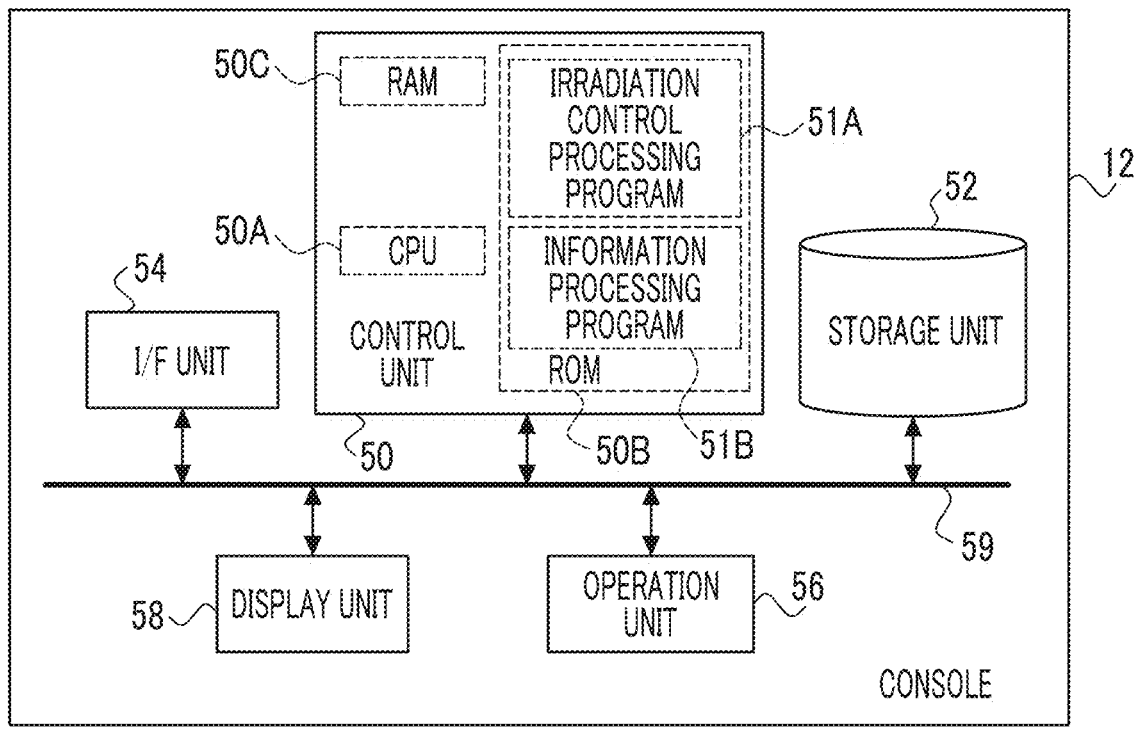
FIG. 3 is a block diagram showing an example of a configuration of a console according to the embodiment.

The console 12 according to the present embodiment is, for example, a server computer. As shown in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other via a bus 59, such as a system bus or a control bus, such that various types of information can be exchanged.

The control unit 50 according to the present embodiment controls an overall operation of the console 12. The control unit 50 comprises a CPU 50A, a ROM 50B, and a RAM 50C. The ROM 50B stores, in advance, various programs including an irradiation control processing program 51A and an information processing program 51B, which are executed by the CPU 50A and will be described below. The RAM 50C transitorily stores various data. The CPU 50A according to the present embodiment is an example of a processor according to the present disclosure. The information processing program 51B according to the present embodiment is an example of an information processing program according to the present disclosure.

The storage unit 52 stores the image data of the radiation image captured by the mammography apparatus 10 or various types of other information. Specific examples of the storage unit 52 include an HDD and an SSD.

The operation unit 56 is used by the user to input the instruction, various types of information, and the like related to the radiation image capturing and the like, including an irradiation instruction of the radiation R. The operation unit 56 is not particularly limited, and examples thereof include various switches, a touch panel, a touch pen, and a mouse. The display unit 58 displays various types of information. It should be noted that the operation unit 56 and the display unit 58 may be integrated to form a touch panel display.

The I/F unit 54 performs communication of various types of information between the mammography apparatus 10 and the RIS 2 by wireless communication or wired communication. The console 12 according to the present embodiment receives the image data of the radiation image captured by the mammography apparatus 10 from the mammography apparatus 10 via the I/F unit 54 by wireless communication or wired communication.

Figure 4:
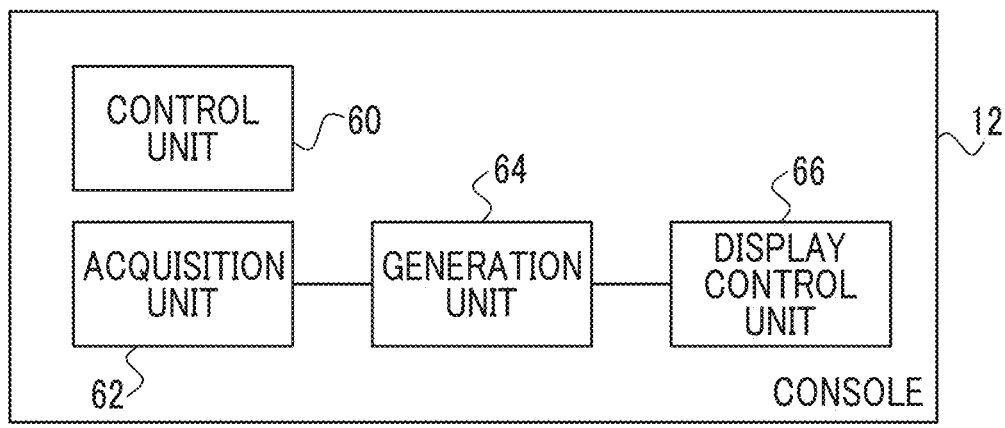
FIG. 4 is a functional block diagram showing an example of a function of the console according to the embodiment.

Further, FIG. 4 shows a functional block diagram of an example of the configuration of the console 12 according to the present embodiment. As shown in FIG. 4, the console 12 comprises a control unit 60. As an example, in the console 12 according to the present embodiment, the CPU 50A of the control unit 50 functions as the control unit 60 by the CPU 50A executing the irradiation control processing program 51A stored in the ROM 50B.

The control unit 60 has a function of performing control related to the irradiation with the radiation R in the mammography apparatus 10 in the contrast imaging. In the present embodiment, in a case of performing the contrast imaging, the radiation image is captured by emitting the radiation having the first energy from the radiation source 37R to the breast in a state in which the contrast medium has been injected. In addition, the radiation image is captured by emitting the radiation having the second energy higher than the first energy from the radiation source 37R to the breast in a state in which the contrast medium has been injected. It should be noted that, in the present embodiment, the radiation image captured by emitting the radiation R having the first energy is referred to as a "low-energy image", and the radiation image captured by emitting the radiation R having the second energy is referred to as a "high-energy image". In addition, in a case in which the images captured by the mammography apparatus 10 are collectively referred to without distinction between types, such as the low-energy image and the high-energy image, the images are simply referred to as the "radiation image".

For example, an iodine contrast medium with a k-absorption edge of 32 keV is generally used as the contrast medium for the contrast imaging. In the contrast imaging in this case, the low-energy image is captured by emitting the radiation R having the first energy lower than the k-absorption edge of the iodine contrast medium. In addition, the high-energy image is captured by emitting the radiation R having the second energy higher than the k-absorption edge of the iodine contrast medium.

Therefore, in the contrast imaging, the control unit 60 according to the present embodiment performs control of emitting the radiation R having the first energy from the radiation source 37R and control of emitting the radiation R having the second energy. In other words, the control unit 60 performs control of causing the mammography apparatus 10 to capture the low-energy image and control of causing the mammography apparatus 10 to capture the high-energy image.

A body tissue, such as a mammary gland, and the contrast medium have different absorption characteristics of the radiation. Therefore, the contrast medium is clearly reflected in the high-energy image captured as described above. In addition, in the low-energy image, almost no contrast medium is reflected, and the body tissue, such as the mammary gland, is clearly reflected. Therefore, the difference image showing a difference between the low-energy image and the high-energy image can be made to be an image in which a mammary gland structure is removed and the contrast medium is clearly reflected.

In addition, in the contrast imaging, changes in a state in which the contrast medium permeates the breast are imaged in time series. For example, the contrast medium tends to more easily permeate in a lesion, such as a tumor, than the mammary gland. Also, as the lesion is more malignant, the contrast medium tends to permeate faster and the contrast medium tends to be washed out faster. Therefore, in the radiography system 1 according to the present embodiment, a temporal change or an amount of permeation (contrast amount) of the contrast medium permeating a region of interest, such as the lesion, is observed by using a plurality of difference images obtained in time series.

In order to obtain the plurality of difference images, in the present embodiment, one of the high-energy image and the low-energy image is captured each time a predetermined time, such as 1 second, elapses. As described above, in order to observe the temporal change of the contrast amount of the region of interest, it is necessary to capture the high-energy image in which the contrast medium is clearly reflected, according to the temporal change. On the other hand, in a case in which the body movement is not taken into consideration, the temporal change of the state of the mammary gland structure, particularly, the temporal change within an imaging time of the contrast imaging is very small, so that the low-energy image does not need to be captured as frequently as the high-energy image, and may be captured, for example, only once. It should be noted that, since the state of the mammary gland structure may be changed due to the body movement of the examinee, the low-energy image may be captured a plurality of times.

Therefore, in the present embodiment, the number of times the low-energy image is captured in one contrast imaging is set to be smaller than the number of times the high-energy image is captured. In addition, an imaging timing of the low-energy image, such as an imaging interval between the low-energy images or a ratio between the number of times of capturing of the low-energy image and the number of times of capturing of the high-energy image, is determined according to the breast which is the subject. As an example, in the present embodiment, the imaging timing of the low-energy image is determined in advance according to a thickness of the breast, a composition of the breast, and an age of the subject. Specifically, as the breast is thicker, the mammary gland structure tends to be likely to be moved with the temporal change even in a compression state. Therefore, as the breast is thicker, the imaging interval between the low-energy images is shorter. Alternatively, the imaging interval between the low-energy images in a case in which the thickness of the breast is equal to or greater than a threshold value is made shorter than the imaging interval between the low-energy images in a case in which the thickness of the breast is smaller than the threshold value. In addition, since the breast is softer as a proportion of fat is increased as the composition of the breast, the mammary gland structure tends to be likely to be moved with the temporal change even in the compression state. Therefore, as the proportion of fat in the breast is higher or as the breast is softer, the imaging interval between the low-energy images is shorter. Alternatively, the imaging interval between the low-energy images in a case in which the proportion of fat in the breast is equal to or greater than a threshold value is made shorter than the imaging interval between the low-energy images in a case in which the proportion of fat is smaller than the threshold value. In addition, as the subject gets older, it is difficult for the subject to maintain the same posture, so that the subject itself tends to be likely to be moved. Therefore, as the subject gets older, the imaging interval between the low-energy images is shorter.

The control unit 60 according to the present embodiment specifies the imaging timing of the low-energy image according to at least one of the thickness of the breast, the composition of the breast, or the age of the subject. In addition, the control unit 60 according to the present embodiment performs control of emitting, from the radiation source 37R, the radiation having the first energy or the second energy based on the specified imaging timing of the low-energy image and the predetermined time for performing the imaging.

Figure 5:
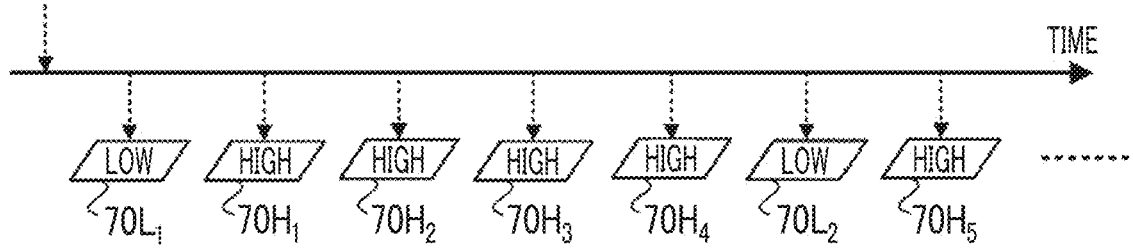
FIG. 5 is a time chart showing an example of imaging timings of a low-energy image and a high-energy image in contrast imaging using the mammography apparatus according to the embodiment.

FIG. 5 shows an example of the imaging timings of the low-energy image and the high-energy image in the contrast imaging by the mammography apparatus 10 according to the present embodiment. In the example shown in FIG. 5, in a case in which the contrast imaging is started, first, a low-energy image 70L (see FIG. 5, $70L_1$) is captured, and then high-energy images 70H (see FIG. 5, $70H_1$ to $70H_4$) are captured each time the predetermined time elapses. Then, in a case in which the specified imaging timing of the low-energy image is reached, the low-energy image 70L (see FIG. 5, $70L_2$) is captured again, and then the high-energy image 70H (see FIG. 5, $70H_5$) is captured each time the predetermined time elapses. In this way, the low-energy image 70L and the high-energy image 70H are repeatedly captured until a contrast imaging time ends.

In addition, the console 12 according to the present embodiment comprises an acquisition unit 62, a generation unit 64, and a display control unit 66. As an example, in the console 12 according to the present embodiment, the CPU 50A of the control unit 50 also functions as the acquisition unit 62, the generation unit 64, and the display control unit 66 by the CPU 50A executing the information processing program 51B stored in the ROM 50B.

The acquisition unit 62 has a function of acquiring the low-energy image and the high-energy image captured by the mammography apparatus 10. Specifically, the acquisition unit 62 acquires image data representing the low-energy image and image data representing the high-energy image captured by the radiation detector 28 of the mammography apparatus 10 via the I/F unit 24 and the I/F unit 54. The acquisition unit 62 outputs the acquired low-energy image and high-energy image to the generation unit 64.

The generation unit 64 has a function of generating a plurality of difference images showing a difference between the low-energy image and each of a plurality of high-energy images. As an example, the generation unit 64 according to the present embodiment generates the difference image between the low-energy image and the plurality of high-energy images captured in a period from capturing of a current low-energy image to capturing of a next low-energy image.

Figure 6A:
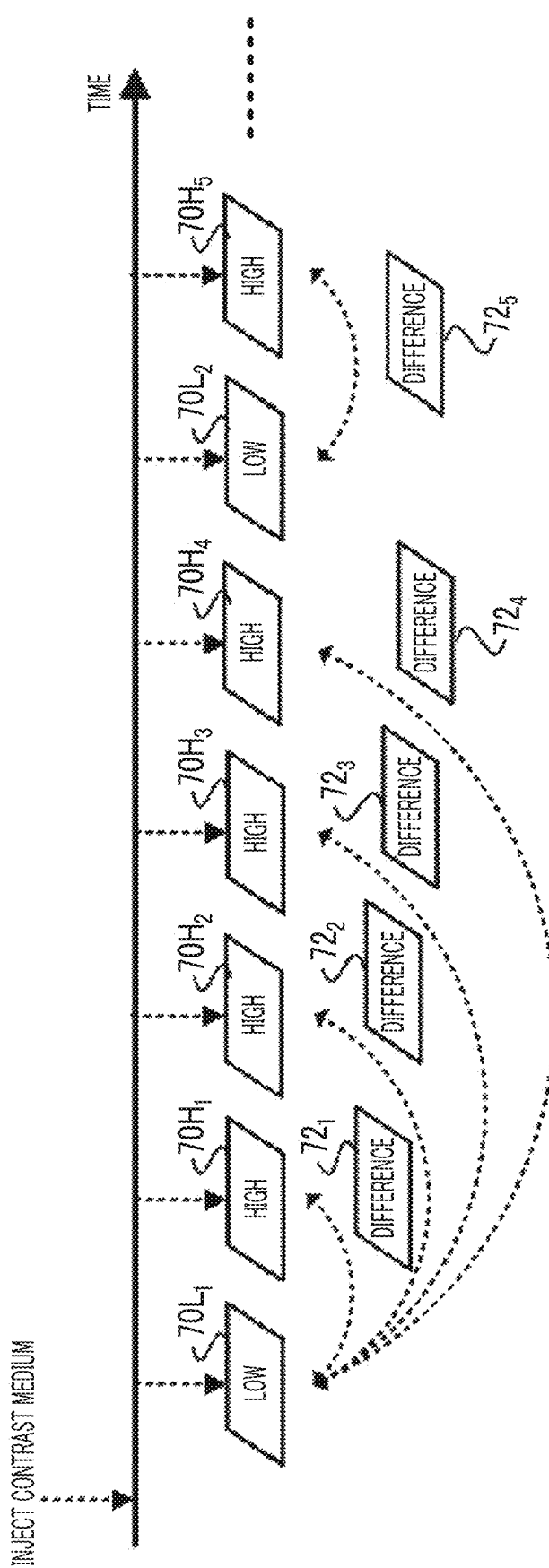
FIG. 6A is a diagram for describing an example of a generation method of a difference image.

As an example, in the present embodiment, the difference image is generated by deriving the difference between the low-energy image and each high-energy image. Specifically, as shown in FIG. 6A, the generation unit 64 generates a difference image $72_1$ between the low-energy image $70L_1$ and the high-energy image $70H_1$. Specifically, the generation unit 64 generates the difference image data representing the difference image in which the mammary gland tissue is removed and the contrast medium is enhanced, by subtracting image data obtained by multiplying the low-energy image $70L_1$ by a predetermined coefficient from image data obtained by multiplying the high-energy image $70H_1$ by a predetermined coefficient for each corresponding pixel. Similarly, the generation unit 64 generates a difference image $72_2$ between the low-energy image $70L_1$ and the high-energy image $70H_2$, generates a difference image $72_3$ between the low-energy image $70L_1$ and the high-energy image $70H_3$, and generates a difference image $72_4$ between the low-energy image $70L_1$ and the high-energy image $70H_4$. In addition, the generation unit 64 generates a difference image $72_5$ between the low-energy image $70L_2$ and the high-energy image $70H_5$.

Figure 6B:
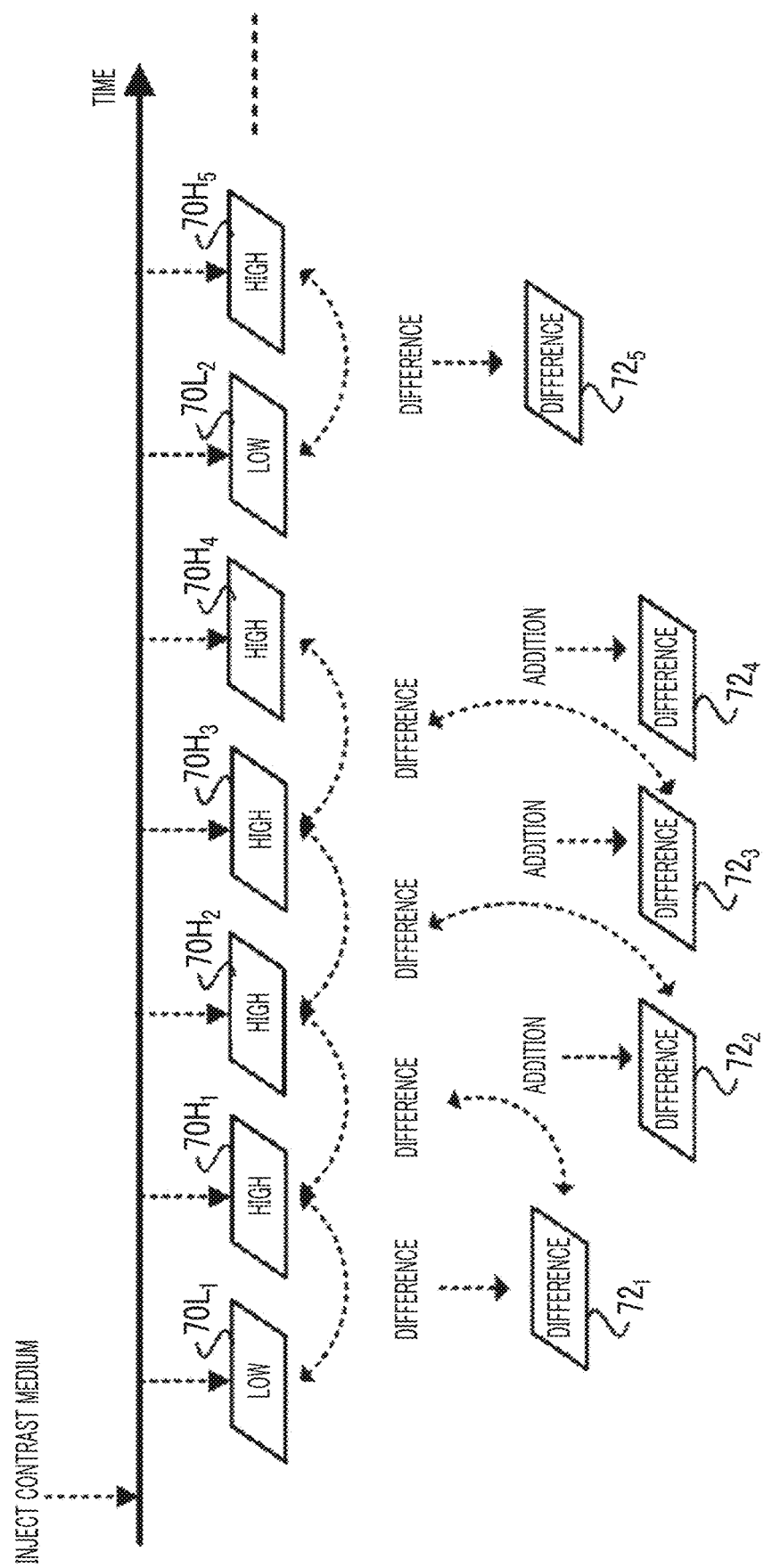
FIG. 6B is a diagram for describing another example of the generation method of the difference image.

It should be noted that a method by which the generation unit 64 generates the difference image is not limited to the method described above. For example, the difference image may be generated by adding a difference between the high-energy images to the difference between the low-energy image and the high-energy image. Specifically, as shown in FIG. 6B, as described above, the generation unit 64 generates the difference image $72_1$ between the low-energy image $70L_1$ and the high-energy image $70H_1$. In addition, the generation unit 64 generates the difference image $72_2$ by adding an image showing a difference between the high-energy image $70H_2$ and the high-energy image $70H_1$ to the difference image $72_1$, generates the difference image $72_3$ by adding an image showing a difference between the high-energy image $70H_3$ and the high-energy image $70H_2$ to the difference image $72_2$, and generates the difference image $72_4$ by adding an image showing a difference between the high-energy image $70H_4$ and the high-energy image $70H_3$ to the difference image $72_3$.

The display control unit 66 has a function of causing the display unit 58 to continuously display the difference images generated by the generation unit 64 as a moving image in a time series order. In the present embodiment, the "moving image" means that still images are displayed one after another at high speed and recognized as the moving image. Therefore, the so-called "frame advance" is also included in the moving image depending on a degree of "high speed" in the display.

In addition, the display control unit 66 according to the present embodiment has a function of deriving each of information indicating the temporal change of the contrast amount of the region of interest in the difference image and information indicating the temporal change of the contrast amount of an outside of the region of interest and displaying the derived information on the display unit 58. It should be noted that a method by which the display control unit 66 specifies the region of interest from the difference image is not particularly limited. For example, the region of interest may be specified from the difference image by receiving information about the region of interest input by the user. Specifically, at least one image of the difference image, the low-energy image, or the high-energy image may be displayed on the display unit 58, and a region designated by the user operating the operation unit 56 on the display image may be received as the information about the region of interest. In addition, for example, the display control unit 66 may specify the region of interest by applying computer aided diagnosis (CAD) to the difference image. It should be noted that a method by which the display control unit 66 specifies the outside of the region of interest from the difference image is not particularly limited. For example, a region excluding the region of interest from the region representing the breast in the difference image may be specified as the outside of the region of interest. In addition, for example, a mammary gland region other than the region of interest may be specified as the outside of the region of interest.

Next, an action of the console 12 in the contrast imaging by the radiography system 1 according to the present embodiment will be described with reference to the drawings.

Figure 7:
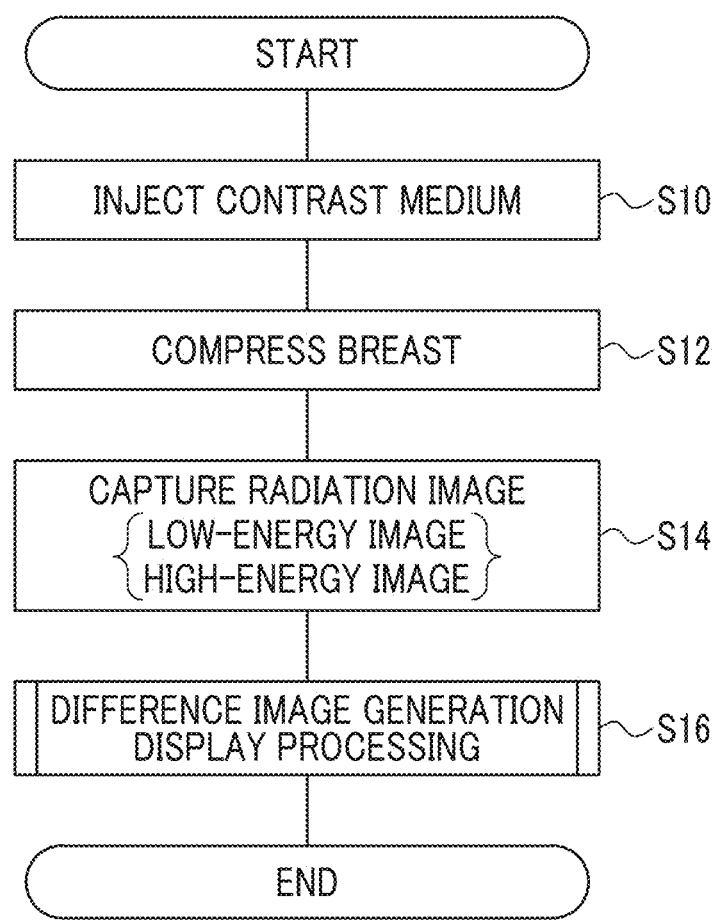
FIG. 7 is a flowchart showing an example of a flow of contrast imaging by the radiography system according to the embodiment.

FIG. 7 shows a flowchart showing an example of a flow of the contrast imaging by the radiography system 1 according to the present embodiment. In a case in which the contrast imaging is performed, first, the user injects the contrast medium into the breast, which is the subject, as shown in step S10 of FIG. 7. Next, as shown in step S12, the user positions the breast of the examinee on the imaging table 30 of the mammography apparatus 10 and compresses the breast with the compression plate 40.

Figure 8:
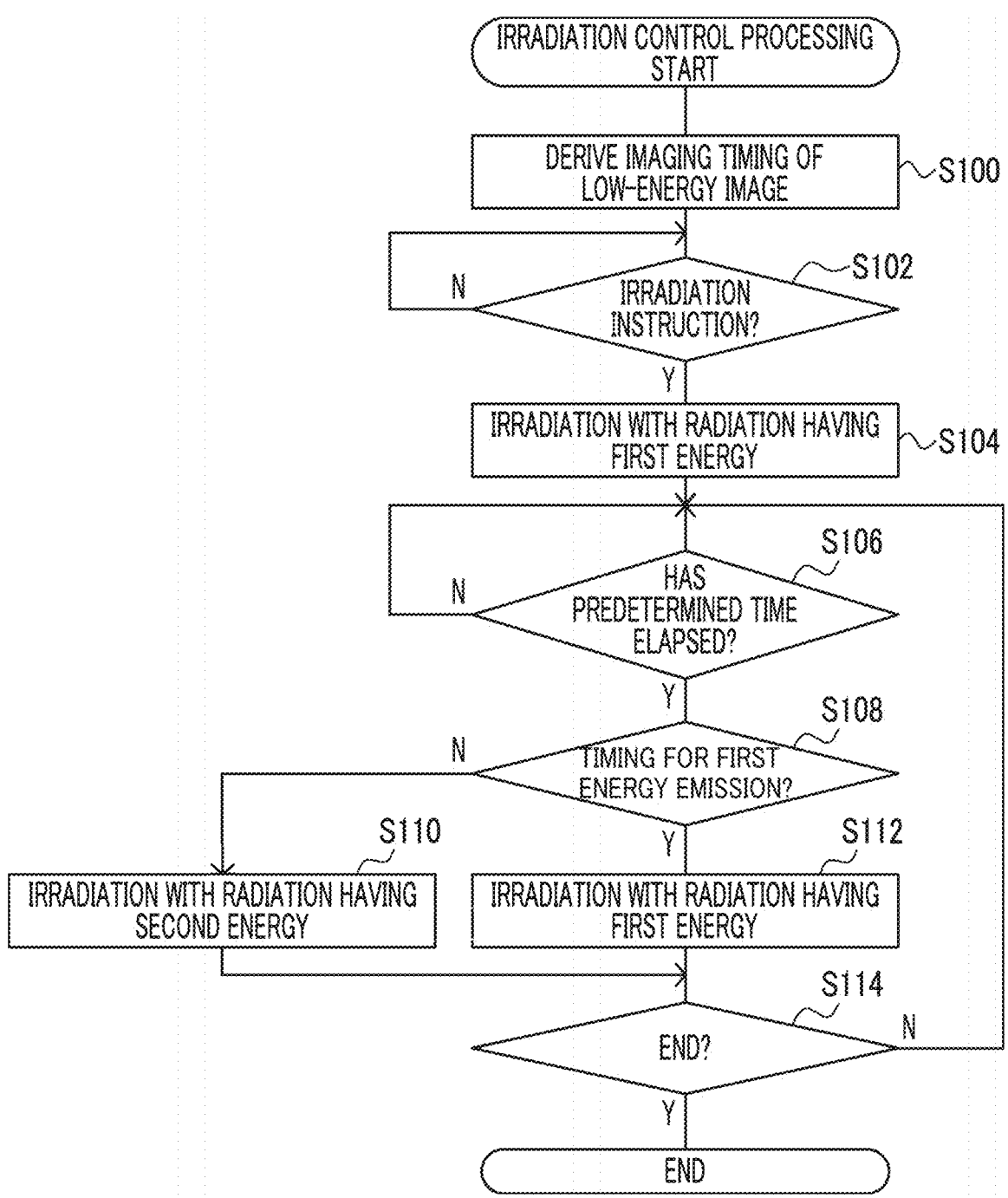
FIG. 8 is a flowchart showing an example of a flow of irradiation control processing executed in the contrast imaging.

Next, in step S14, the mammography apparatus 10 captures the radiation image, specifically, the low-energy image and the high-energy image. In the present embodiment, as described above, the control unit 60 of the console 12 performs control related to the irradiation with the radiation R in the mammography apparatus 10. As an example, in the console 12 according to the present embodiment, the CPU 50A of the control unit 50 executes the irradiation control processing program 51A stored in the ROM 50B to execute irradiation control processing shown in FIG. 8 as an example. FIG. 8 shows a flowchart showing an example of a flow of the irradiation control processing executed in the console 12 according to the present embodiment.

In step S100 of FIG. 8, the control unit 60 derives the imaging timing of the low-energy image. As described above, in the present embodiment, the imaging timing of the low-energy image is determined in advance according to the thickness of the breast, the composition of the breast, and the age of the subject. Therefore, the control unit 60 acquires breast information indicating at least one of the thickness of the breast, the composition of the breast, or the age of the subject. It should be noted that a method by which the control unit 60 acquires the breast information is not limited. For example, the breast information may be acquired from RIS 2 or the like. In addition, for example, the breast information input by the user may be acquired by the operation unit 56. In addition, for example, in a case in which there is the radiation image captured in the past by the general imaging for the breast of the subject, the control unit 60 may acquire the breast information as an analysis result of analysis of a mammary gland mass or the like from the radiation image obtained by the general imaging. The control unit 60 acquires the information about the imaging timing of the low-energy image, which is associated with the breast information acquired in this way in advance, to derive the imaging timing of the low-energy image.

In next step S102, the control unit 60 determines whether or not the irradiation instruction of the radiation R is received. A negative determination is made in the determination in step S102 until the irradiation instruction is received. On the other hand, in a case in which the irradiation instruction is received, a positive determination is made in the determination in step S102, and the processing proceeds to step S104.

In step S104, the control unit 60 outputs an instruction to perform the irradiation with the radiation R having the first energy to the mammography apparatus 10. In the mammography apparatus 10, the control unit 20 emits the radiation R having the first energy from the radiation source 37R toward the breast based on the instruction input from the console 12, and the low-energy image is captured by the radiation detector 28.

In next step S106, the control unit 60 determines whether or not a predetermined time has elapsed. A negative determination is made in the determination in step S106 until the predetermined time elapses. On the other hand, in a case in which the predetermined time has elapsed, a positive determination is made in the determination in step S106, and the processing proceeds to step S108.

In step S108, the control unit 60 determines whether or not it is a timing for emitting the radiation R having the first energy. Until the imaging timing of the low-energy image derived in step S100 is reached, a negative determination is made in the determination in step S108, and the processing proceeds to step S110.

In step S110, the control unit 60 outputs an instruction to perform the irradiation with the radiation R having the second energy to the mammography apparatus 10, and then proceeds to step S114. In the mammography apparatus 10, the control unit 20 emits the radiation R having the second energy from the radiation source 37R toward the breast based on the instruction input from the console 12, and the high-energy image is captured by the radiation detector 28.

On the other hand, in a case in which the imaging timing of the low-energy image is reached in step S108, a positive determination is made, and the processing proceeds to step S112. In step S112, the control unit 60 outputs the instruction to perform the irradiation with the radiation R having the first energy to the mammography apparatus 10 as in step S104, and then proceeds to step S114. As described above, in the mammography apparatus 10, the low-energy image is captured.

In step S114, the control unit 60 determines whether or not to end the present irradiation control processing. Until a predetermined end condition is satisfied, a negative determination is made in the determination in step S114, the processing returns to step S106, and the processing of steps S106 to S112 is repeated. On the other hand, in a case in which the end condition is satisfied, a positive determination is made in the determination in step S114, and the present irradiation control processing ends. It should be noted that the end condition is not limited. The end condition may be, for example, a condition in which the processing ends in a case in which an elapsed time from the injection of the contrast medium into the breast has passed a predetermined time, in a case in which an elapsed time from the start of the irradiation with the radiation R has passed a predetermined time, in a case in which the number of times of capturing of the radiation image reaches a predetermined number of times, and in a case in which an instruction to end the imaging is received from the user.

In addition, the control unit 60 may end the present irradiation control processing in a case in which the analysis result of the captured radiation image satisfies the end condition. Examples of the end condition in this case include a case in which the contrast amount is not changed. Specifically, the end condition may be a condition in which the processing ends in a case in which the difference between the high-energy images is equal to or smaller than the threshold value, particularly, in a case in which the difference between pixel values of the region of interest in the high-energy images is equal to or smaller than the threshold value.

In this way, in a case in which the irradiation control processing shown in FIG. 8 ends, the contrast imaging ends, and the processing of step S14 shown in FIG. 7 ends.

Figure 9:
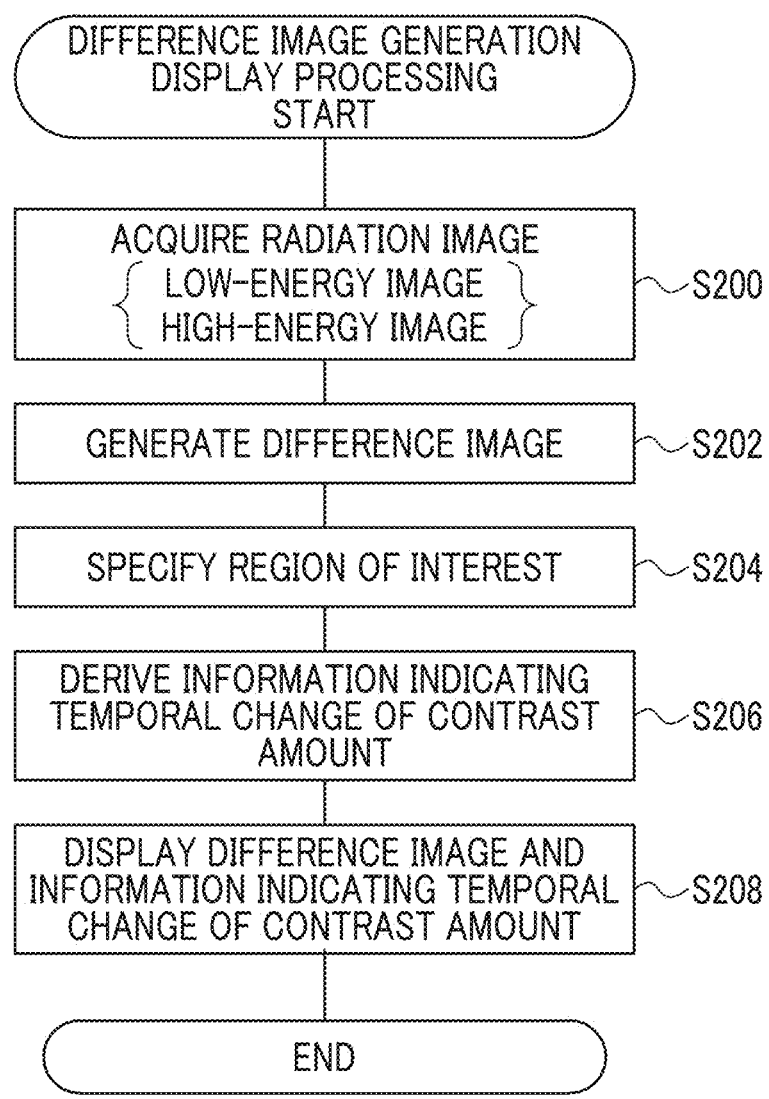
FIG. 9 is a flowchart showing an example of a flow of difference image generation display processing executed in the contrast imaging.

In next step S16, the console 12 performs difference image generation display processing shown in FIG. 9. As an example, in the console 12 according to the present embodiment, the CPU 50A of the control unit 50 executes the information processing program 51B stored in the ROM 50B to execute the difference image generation display processing shown in FIG. 9 as an example. FIG. 9 shows a flowchart showing an example of a flow of the difference image generation display processing executed in the console 12 according to the present embodiment.

In step S200, as described above, the acquisition unit 62 acquires the low-energy image and the high-energy image captured by the contrast imaging from the mammography apparatus 10. It should be noted that a timing at which the acquisition unit 62 acquires the low-energy image and the high-energy image is not limited. For example, the low-energy image and the high-energy image may be acquired from the mammography apparatus 10 each time each of the low-energy image and the high-energy image is captured. In addition, for example, the low-energy image and the high-energy image stored in the storage unit 22 of the mammography apparatus 10 may be acquired after capturing all the low-energy images and the high-energy images ends. In addition, an order of acquiring the low-energy image and the high-energy image is not limited.

In next step S202, as described above, the generation unit 64 generates the plurality of difference images from the low-energy image and the high-energy image acquired in step S200. In next step S204, the display control unit 66 specifies the region of interest from the difference image, as described above.

In next step S206, as described above, the display control unit 66 derives the information indicating the temporal change of the contrast amount. Specifically, the display control unit 66 derives the information indicating the temporal change of the contrast amount of the region of interest specified in step S204 in the difference image generated in step S202. In addition, the display control unit 66 derives the information indicating the temporal change of the contrast amount of the outside of the region of interest specified in step S204 in the difference image generated in step S202. It should be noted that the display control unit 66 may not derive the contrast amount itself. For example, a brightness value of the pixel in the difference image is changed according to the contrast amount. Therefore, the information indicating the temporal change of the brightness value of the difference image may be used as the information indicating the temporal change of the contrast amount.

Figure 10:
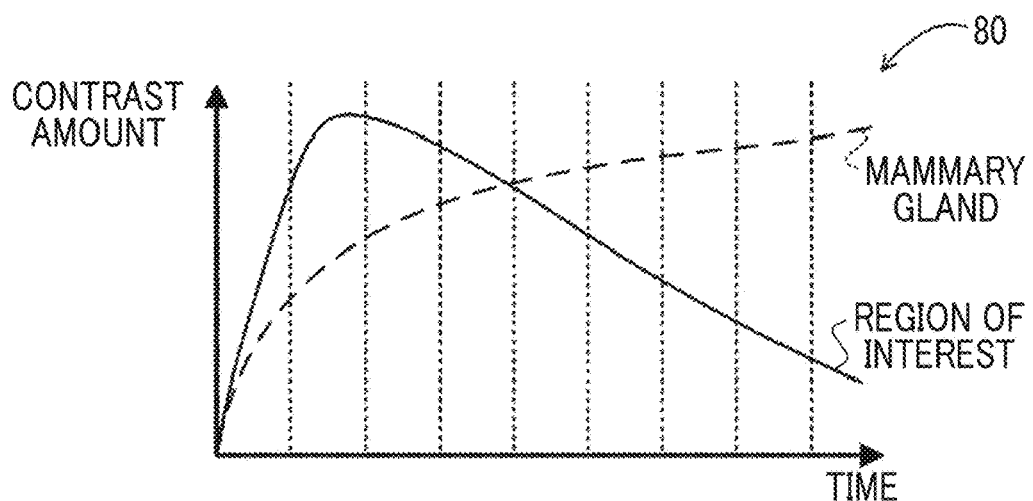
FIG. 10 is a diagram showing an example of information indicating a temporal change of a contrast amount.

FIG. 10 shows an example of information 80 indicating the temporal change of the contrast amount. In the information shown in FIG. 10, the horizontal axis represents the lapse of time since the contrast medium has been injected. In addition, the vertical axis represents the contrast amount. It should be noted that, as described above, the contrast amount in this case may not be the contrast amount itself, but may be the brightness value of the pixel. In the information shown in FIG. 10, a solid line shows an example of the temporal change of the contrast amount in a case in which the region of interest is a tumor, that is, a breast cancer. In addition, an example of the temporal change in the mammary gland region as the outside of the region of interest is shown by a dotted line. As shown in FIG. 10, in a case of the tumor, the contrast medium rapidly permeates and the contrast medium is washed out faster. Therefore, by observing the temporal change of the contrast amount of the region of interest, it can be used as an index for diagnosing whether or not the region of interest is the tumor and whether or not the region of interest is malignant. In addition, although there are individual differences in how the contrast medium is dyed, by comparing the temporal change of the contrast amount of the region outside the region of interest, for example, the mammary gland region assumed to be normal with the temporal change of the contrast amount of the region of interest, the speed at which the contrast medium permeates and the speed at which the contrast medium is washed out can be made clearer.

In next step S208, the display control unit 66 performs control of displaying, on the display unit 58, the plurality of difference images generated in step S202 and the information 80 indicating the temporal change of the contrast amount derived in step S206, and then the present difference image generation display processing ends. It should be noted that the display control unit 66 performs control of performing predetermined image processing of assisting the user in interpreting the image, such as gradation enhancement processing or frequency enhancement processing, on the plurality of difference images generated in step S202 and displaying the plurality of difference images which have been subjected to the image processing on the display unit 58.

Figure 11:
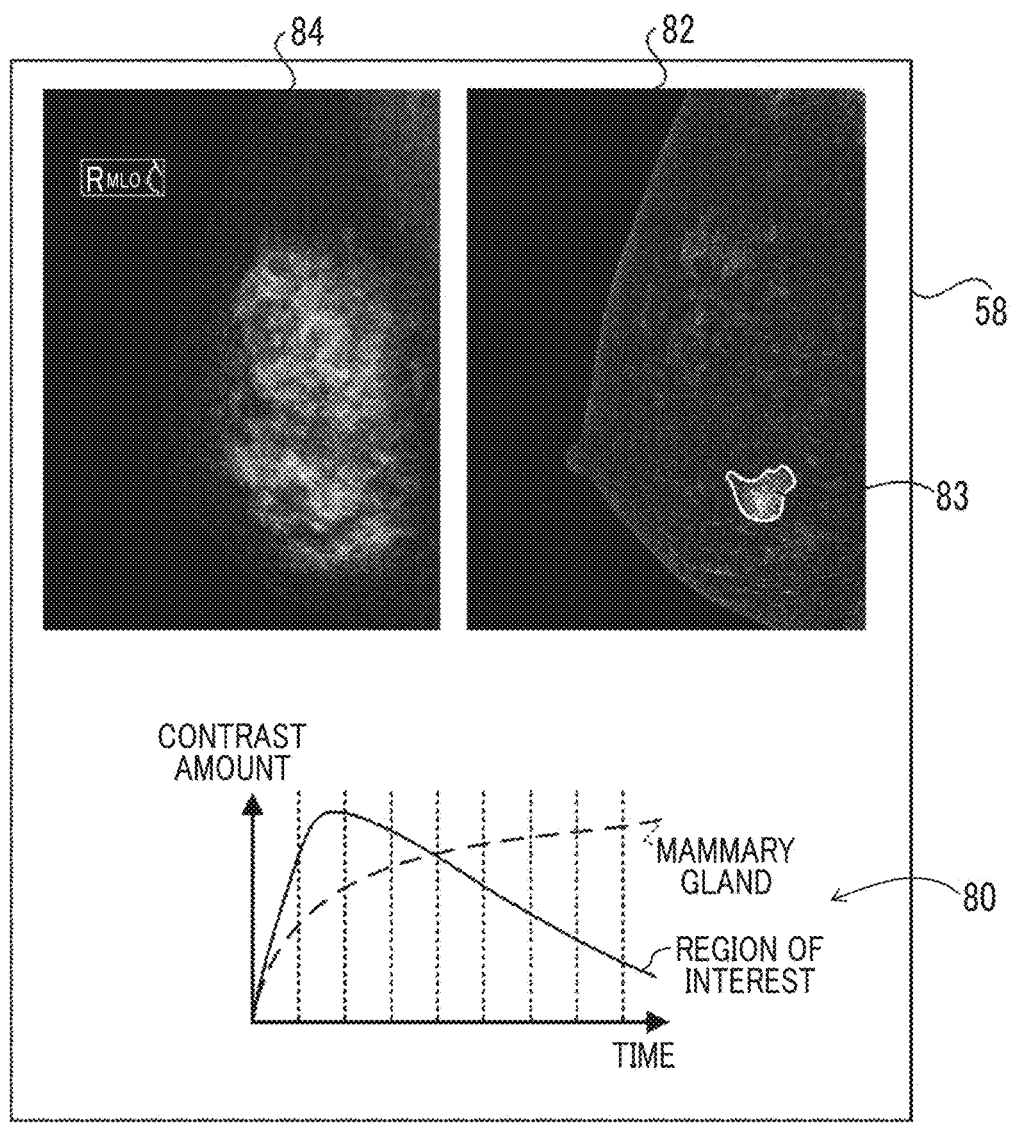
FIG. 11 is a diagram showing an example of a state in which the difference image and the information indicating the temporal change of the contrast amount are displayed on a display unit.

FIG. 11 shows an example of a state in which a moving image 82 and the information 80 indicating the temporal change of the contrast amount are displayed on the display unit 58. As described above, the display control unit 66 according to the present embodiment continuously displays, on the display unit 58, the plurality of difference images as the moving image 82 in the time series order of capturing. In the example shown in FIG. 11, positional information 83 indicating a position of the region of interest is also displayed on the difference image as the moving image 82.

It should be noted that, in a case in which the moving image 82 is displayed, a timing for displaying the next difference image may be changed according to a contrast value of the region of interest. For example, in a case in which the contrast value of the region of interest is equal to or greater than a threshold value, the timing for displaying the next difference image may be delayed, that is, the display speed of the moving image may be made slower than in a case in which the contrast value is smaller than the threshold value. In addition, the display speed of the moving image 82 may be adjustable by the user.

It should be noted that the difference image displayed by the display control unit 66 is not limited to a form of the moving image 82. For example, a form may be adopted in which, among the plurality of difference images generated by the generation unit 64, a difference image having a highest contrast of the region of interest is displayed. In addition, for example, a form may be adopted in which, by displaying a radiation image 84 described below or the low-energy image, the difference image having the highest contrast of a region designated by the user on the radiation image 84 or the low-energy image is displayed.

In addition, as shown in FIG. 11, the display control unit 66 according to the present embodiment also displays the radiation image 84 on the display unit 58 as a comparative example in a case in which there is the radiation image 84 captured by the general imaging for the breast which is the subject, in other words, the radiation image 84 captured in a state in which the contrast medium has not been injected. It should be noted that, in the example shown in FIG. 11, the form has been described in which the moving image 82 and the radiation image 84 are displayed side by side, a form may be adopted in which any one of the moving image 82 or the radiation image 84 is displayed and the image to be displayed is switched according to the instruction of the user.

It should be noted that the radiation image displayed by the display control unit 66 on the display unit 58 is not limited to the image described above. For example, a form may be adopted in which, in addition to the difference image, at least one of the low-energy image or the high-energy image is displayed.

In addition, the image and the information displayed by the display control unit 66 on the display unit 58 are not limited to the image and the information described above. For example, a numerical value indicating the contrast amount of the region of interest may be displayed. In this case, the contrast amount may be the contrast amount of the entire region of interest, or may be any of an average value, a median value, or a maximum value of the contrast amount of the region of interest.

In this way, in a case in which the difference image generation display processing shown in FIG. 9 ends, the difference image generation display processing in step S16 shown in FIG. 7 ends. As a result, the series of processing related to the contrast imaging in the radiography system 1 according to the present embodiment ends. It should be noted that a form may be adopted in which the low-energy image and the plurality of high-energy images, which are captured by the mammography apparatus 10 according to the present embodiment, the plurality of difference images, the moving image 82, and the information 80 indicating the temporal change of the contrast amount, which are generated by the console 12, and the like are stored in the storage unit 52 of the console 12, picture archiving and communication systems (PACS), or the like.

In addition, in each form described above, the form has been described in which the difference image generation display processing is continuously performed after the contrast imaging which is the processing of S14 in FIG. 7 ends, but the timing for performing the difference image generation display processing, that is, the timing for generating the difference image or displaying the difference image is not limited to the present form. For example, a form may be adopted in which the timing of each of the generation of the difference image and the display of the difference image is a timing according to the user's desire after the contrast imaging.

As described above, the console 12 of each form described above comprises the CPU 50A as at least one processor. The CPU 50A acquires the low-energy image captured by the mammography apparatus 10 by emitting the radiation R having the first energy to the breast into which the contrast medium has been injected, and each of the plurality of high-energy images captured by the mammography apparatus 10 at different timings by emitting the radiation R having the second energy higher than the first energy to the breast into which the contrast medium has been injected. In addition, the CPU 50A generates the plurality of difference images showing the difference between the low-energy image and each of the plurality of high-energy images.

As described above, with the console 12 according to the present embodiment, since one low-energy image is applied to the plurality of high-energy images to generate the difference image, it is possible to observe the temporal change of the contrast amount with a smaller number of radiation images. In addition, the radiation R having high energy is easily transmitted through fat, and an exposure dose of the subject is reduced as compared with the radiation R having low energy. Therefore, according to the present embodiment, the number of times of capturing of the low-energy image can be made smaller than the number of times of capturing of the high-energy image, so that the exposure dose of the subject can be reduced.

Figure 12:
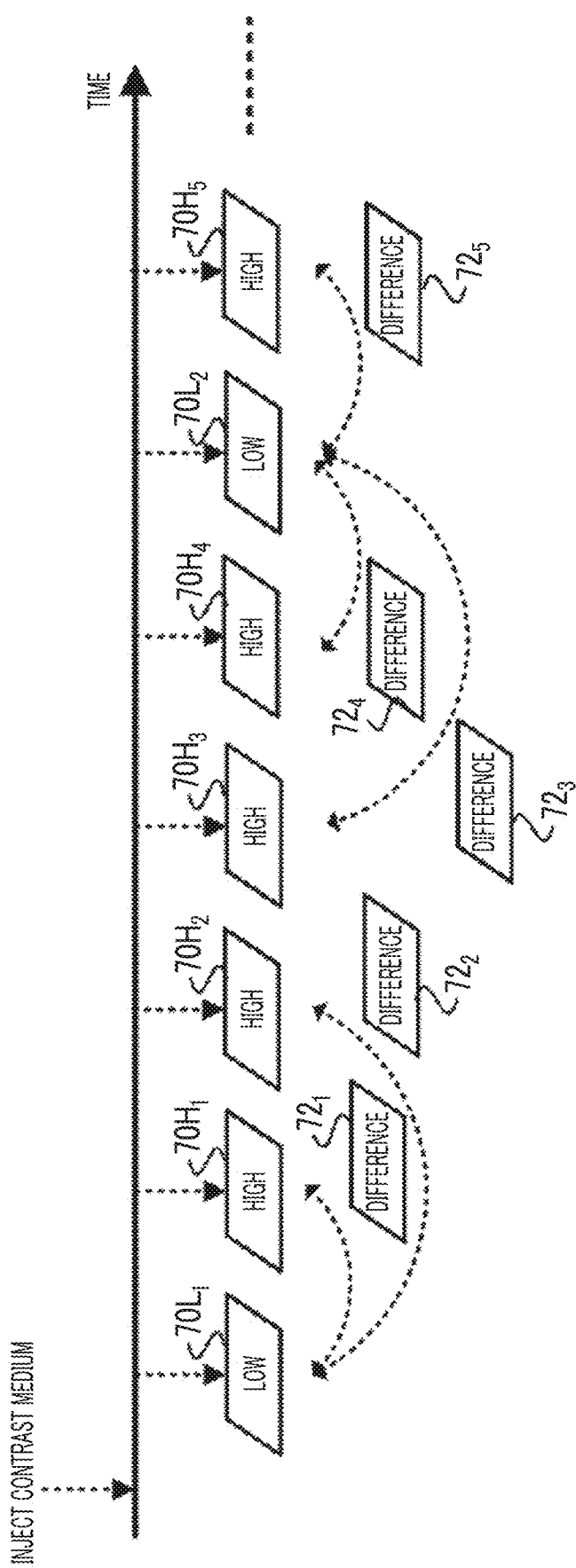
FIG. 12 is a diagram for describing still another example of the generation method of the difference image.

It should be noted that, in the form described above, as shown in FIGS. 6A and 6B, the form has been described in which the generation unit 64 generates the difference image between the low-energy image and the high-energy images captured before the next low-energy image is captured, but a combination of the low-energy image and the high-energy image for generating the difference image is not limited to the present form. For example, a form may be adopted in which the difference image with the low-energy image having the imaging timing closest to the high-energy image is generated. Specifically, as shown in FIG. 12, the generation unit 64 generates the difference image $72_1$ between the high-energy image $70H_1$ and the low-energy image $70L_1$, and generates the difference image $72_2$ between the high-energy image $70H_2$ and the low-energy image $70L_1$. In addition, the generation unit 64 generates the difference image $72_3$ between the high-energy image $70H_3$ and the low-energy image $70L_2$, generates the difference image $72_4$ of the high-energy image $70H_4$ and the low-energy image $70L_2$, and generates the difference image $72_5$ between the high-energy image $70H_5$ and the low-energy image $70L_2$. In this way, the influence of the body movement can be further reduced by generating the difference image by combining the low-energy image having the imaging timing closest to the high-energy image.

In addition, in the form described above, the form has been described in which the low-energy image is first captured in the contrast imaging, but the present disclosure is not limited to the present form, and a form may be adopted in which the high-energy image is captured first.

In addition, in the form described above, the form has been described in which the breast is applied as an example of the subject according to the present disclosure, and the mammography apparatus 10 is applied as an example of the radiography apparatus according to the present disclosure, but the subject is not limited to the breast, and the radiography apparatus is not limited to the mammography apparatus. For example, the subject may be a chest, an abdomen, or the like, and a form may be adopted in which a radiography apparatus other than the mammography apparatus is applied as the radiography apparatus.

In addition, in the form described above, the form has been described in which the console 12 is an example of the information processing apparatus according to the present disclosure, but an apparatus other than the console 12 may have the function of the information processing apparatus according to the present disclosure. In other words, some or all of the functions of the control unit 60, the acquisition unit 62, the generation unit 64, and the display control unit 66 may be provided in an apparatus other than the console 12, for example, the mammography apparatus 10 or an external apparatus.

In addition, in the form described above, various processors shown below can be used as the hardware structure of processing units that execute various pieces of processing, such as the control unit 60, the acquisition unit 62, the generation unit 64, and the display control unit 66. As described above, the various processors include, in addition to the CPU which is a general-purpose processor which executes software (program) and functions as various processing units, a programmable logic device (PLD) which is a processor of which a circuit configuration can be changed after manufacture, such as a field programmable gate array (FPGA), and a dedicated electric circuit which is a processor having a circuit configuration which is designed for exclusive use in order to execute specific processing, such as an application specific integrated circuit (ASIC).

One processing unit may be composed of one of the various processors or may be composed of a combination of two or more processors of the same type or different types (for example, a combination of a plurality of FPGAs or a combination of a CPU and an FPGA). In addition, a plurality of processing units may be composed of one processor.

A first example of the configuration in which the plurality of processing units are composed of one processor is a form in which one processor is composed of a combination of one or more CPUs and software and the processor functions as the plurality of processing units, as represented by the computer, such as a client and a server. Second, as represented by a system on chip (SoC) or the like, there is a form of using a processor that realizes the function of the entire system including the plurality of processing units by one integrated circuit (IC) chip. As described above, various processing units are composed of one or more of the various processors as the hardware structure.

Further, more specifically, an electric circuit (circuitry) obtained by combining circuit elements, such as semiconductor elements, can be used as the hardware structure of the various processors.

In addition, in each embodiment described above, the aspect has been described in which the irradiation control processing program 51A and the information processing program 51B are stored (installed) in advance in the ROM 50B, but the present disclosure is not limited to this. Each of the irradiation control processing program 51A and the information processing program 51B may be provided in a form being recorded in the recording medium, such as a compact disc read only memory (CD-ROM), a digital versatile disc read only memory (DVD-ROM), and a universal serial bus (USB) memory. In addition, a form may be adopted in which each of the irradiation control processing program 51A and the information processing program 51B is downloaded from an external apparatus via a network.

The disclosure of JP2020-162694 filed on Sep. 28, 2020 is incorporated in the present specification by reference in its entirety.

All documents, patent applications, and technical standards described in the present specification are incorporated in the present specification by reference to the same extent as a case in which each document, patent application, and technical standard are specifically and individually noted to be incorporated by reference.

What is claimed is:

1. An information processing apparatus comprising:
at least one processor that is configured to:
acquire a low-energy image captured by a radiography apparatus by emitting radiation having first energy to a subject into which a contrast medium has been injected, and each of a plurality of high-energy images captured by the radiography apparatus at different timings by emitting radiation having second energy higher than the first energy to the subject into which the contrast medium has been injected,
generate a plurality of difference images showing a difference between the low-energy image and each of the plurality of high-energy images,
acquire, as the low-energy image, a plurality of low-energy images captured by the radiography apparatus at different timings, which are smaller than in capturing of the plurality of high-energy images, and
generate a difference image showing a difference between each of the plurality of high-energy images and a low-energy image satisfying a predetermined condition among the plurality of low-energy images.

2. The information processing apparatus according to claim 1,
wherein the at least one processor is configured to continuously display the plurality of difference images as a moving image in a time series order of capturing.

3. The information processing apparatus according to claim 1,
wherein the at least one processor is configured to display a difference image having a highest contrast of a region of interest among the plurality of difference images.

4. The information processing apparatus according to claim 1,
wherein the at least one processor is configured to:
derive a contrast amount of a region of interest in each of the plurality of difference images, and
generate information indicating a temporal change of the contrast amount of the region of interest and displays the generated information.

5. The information processing apparatus according to claim 4,
wherein the at least one processor is configured to:
derive a contrast amount of a region outside the region of interest in each of the plurality of difference images, and
generate information indicating a temporal change of the contrast amount of the region outside the region of interest and displays the generated information.

6. The information processing apparatus according to claim 4,
wherein the at least one processor is configured to:
receive information indicating the region of interest or information indicating a region outside the region of interest, and
derive the contrast amount based on the received information.

7. The information processing apparatus according to claim 1,
wherein the predetermined condition is a condition in which an imaging timing is closest to an imaging timing of the high-energy image.

8. The information processing apparatus according to claim 1,
wherein an imaging interval between the plurality of low-energy images is determined according to the subject.

9. The information processing apparatus according to claim 1,
wherein a ratio between the number of the plurality of low-energy images and the number of the plurality of high-energy images is determined according to the subject.

10. The information processing apparatus according to claim 1,
wherein the at least one processor is configured to:
generate a first difference image showing a difference between the low-energy image and a high-energy image having an imaging timing closest to an imaging timing of the low-energy image,
generate a second difference image showing a difference between the high-energy images, and
generate the plurality of difference images by using the first difference image and the second difference image.

11. The information processing apparatus according to claim 1,
wherein the subject is a breast, and
the radiography apparatus is a mammography apparatus.

12. An information processing method executed by a computer, the method comprising:
acquiring a low-energy image captured by a radiography apparatus by emitting radiation having first energy to a subject into which a contrast medium has been injected, and each of a plurality of high-energy images captured by the radiography apparatus at different timings by emitting radiation having second energy higher than the first energy to the subject into which the contrast medium has been injected;
generating a plurality of difference images showing a difference between the low-energy image and each of the plurality of high-energy images;
acquiring, as the low-energy image, a plurality of low-energy images captured by the radiography apparatus at different timings, which are smaller than in capturing of the plurality of high-energy images; and
generating a difference image showing a difference between each of the plurality of high-energy images and a low-energy image satisfying a predetermined condition among the plurality of low-energy images.

13. A non-transitory storage medium storing a program executable by a computer to perform information processing, the information processing comprising:
- acquiring a low-energy image captured by a radiography apparatus by emitting radiation having first energy to a subject into which a contrast medium has been injected, and each of a plurality of high-energy images captured by the radiography apparatus at different timings by emitting radiation having second energy higher than the first energy to the subject into which the contrast medium has been injected;
- generating a plurality of difference images showing a difference between the low-energy image and each of the plurality of high-energy images;
- acquiring, as the low-energy image, a plurality of low-energy images captured by the radiography apparatus at different timings, which are smaller than in capturing of the plurality of high-energy images; and
- generating a difference image showing a difference between each of the plurality of high-energy images and a low-energy image satisfying a predetermined condition among the plurality of low-energy images.

\* \* \* \* \*